United States Patent [19]

Chen et al.

[11] Patent Number: 5,686,369
[45] Date of Patent: Nov. 11, 1997

[54] METHOD AND APPARATUS FOR TREATING DEHYDROGENATION CATALYSTS

[75] Inventors: Shiou-Shan Chen, Winchester; Shyh-Yuan Hwang, Cambridge; Slawomir A. Oleksy, Billerica; Sanjeev Ram, Hingham, all of Mass.

[73] Assignee: Raytheon Engineers & Constructors, Inc., Lexington, Mass.

[21] Appl. No.: 467,301

[22] Filed: Jun. 6, 1995

Related U.S. Application Data

[62] Division of Ser. No. 88,306, Jul. 7, 1993, Pat. No. 5,461,179.

[51] Int. Cl.$^6$ .................. B01J 38/06; B01J 38/64
[52] U.S. Cl. .................. 502/25; 502/34; 502/55
[58] Field of Search .................. 502/55, 25, 34

[56] References Cited

U.S. PATENT DOCUMENTS

| | | | |
|---|---|---|---|
| 3,755,482 | 8/1973 | Nunnally et al. | 585/441 |
| 4,064,187 | 12/1977 | Soderquist et al. | 260/669 R |
| 4,277,369 | 7/1981 | Courty et al. | 252/415 |
| 4,287,375 | 9/1981 | Moller et al. | 585/440 |
| 4,451,686 | 5/1984 | DeClippeleir et al. | 585/444 |
| 4,551,571 | 11/1985 | Sarumaru et al. | 585/440 |
| 4,590,324 | 5/1986 | Satek | 585/444 |
| 4,645,753 | 2/1987 | Zletz et al. | 502/202 |
| 4,737,595 | 4/1988 | Jones et al. | 585/654 |
| 4,902,845 | 2/1990 | Kim et al. | 585/486 |
| 5,190,906 | 3/1993 | Murakami et al. | 502/304 |
| 5,461,179 | 10/1995 | Chen et al. | 585/440 |

FOREIGN PATENT DOCUMENTS

| | | |
|---|---|---|
| 298353 | 2/1992 | Germany. |
| 298354 | 2/1992 | Germany. |
| 298355 | 2/1992 | Germany. |
| 298356 | 2/1992 | Germany. |
| 298357 | 2/1992 | Germany. |

*Primary Examiner*—Glenn Caldarola
*Assistant Examiner*—Alexander G. Ghyka
*Attorney, Agent, or Firm*—Lappin & Kusmer LLP

[57] ABSTRACT

A method and apparatus are disclosed for regenerating and/or stabilizing the activity of a dehydrogenation catalyst used in dehydrogenating an alkylaromatic hydrocarbon to obtain an alkenylaromatic hydrocarbon, the method comprising the steps of continuously or intermittently adding to a reactant stream an effective amount of an alkali metal compound without interrupting the dehydrogenation reaction.

56 Claims, 1 Drawing Sheet

METHOD AND APPARATUS FOR TREATING DEHYDROGENATION CATALYSTS

This is a divisional of application Ser. No. 08/088,306 filed on Jul. 7, 1993, now U.S. Pat. No. 5,461,179.

The present invention relates generally to a method and apparatus for greatly extending the useful life of a catalyst bed used in the catalytic dehydrogenation of alkylaromatic hydrocarbons while maintaining a very high level of conversion and a very high level of selectivity and without the need to interrupt the conversion process.

BACKGROUND OF THE INVENTION

It is known in the art that an alkylaromatic hydrocarbon can be catalytically dehydrogenated to form an alkenylaromatic hydrocarbon, such as in the conversion of ethylbenzene to styrene. The prior art teaches a variety of different dehydrogenation catalysts and process parameters, each having different advantages and disadvantages. In general, the prior art teaches that certain tradeoffs ordinarily must be made between level of conversion and level of selectivity, between level of conversion and catalyst life, and so forth. For example, the disadvantage of obtaining a higher degree of dehydrogenation of the alkylaromatic in some processes may be a lower level of selectivity, i.e., a higher percentage of undesired dehydrogenation byproducts. Obviously, it is most advantageous and cost-effective to obtain both high levels of conversion and high levels of selectivity, if possible.

Catalyst life, and the related cost factors, is another important process parameter in these dehydrogenation reactions. First are the costs related to the catalyst itself. Although the unit cost of the catalyst may not be great, because of the large amounts of catalyst required as well as the cost of disposing of used, contaminated catalyst in an environmentally acceptable way, the life of the catalyst and the ability to regenerate used catalyst are critical elements in a commercial dehydrogenation process. Second are the costs related to shutting down a large, perhaps multistage, dehydrogenation reactor, operating at temperatures on the order of 600° C., in order to either replace or regenerate the catalyst bed. In addition to the obvious labor costs, there are also the capital costs of having expensive equipment off-line for any length of time. Heat losses add still further costs to this catalyst replacement or regeneration step. Of even greater significance is the cost of lost production during the shutdown period.

Thus, on the one hand, it is preferred to maximize catalyst life. But, on the other hand, normal catalyst degeneration during use tends to reduce the level of conversion, the level of selectivity, or both, resulting in an undesirable loss of process efficiency. Various possible explanations for the typical degeneration of dehydrogenation catalysts during use are found in the literature. These include carbonization of catalyst surfaces, physical breakdown of the interstitial structures of the catalysts, loss of catalization promoters, and others. Depending on the catalyst and the various process parameters, one or more of these mechanisms, or other mechanisms not yet identified, may be at work.

Although the prior art teaches various methods for regenerating used catalyst in order to restore temporarily and only partially the catalyst's effectiveness, these methods generally involve stopping the dehydrogenation, shutting down the dehydrogenation reactor or, in some cases, removing the catalyst for external regeneration. Furthermore, the process impact of such periodic catalyst regeneration is an undesirable saw-tooth pattern of output: levels of conversion and selectivity start out relatively high but slowly and continuously deteriorate until the point where the catalyst is regenerated to restore a relatively high level of conversion and selectivity. But, immediately thereafter, catalyst effectiveness begins again to deteriorate. As a result, it is not possible utilizing conventional catalyst regeneration methods to achieve steady-state process conditions at high levels of conversion and selectivity.

For example, German Patentschrift Nos. DD 298 353, DD 298 354, DD 298 355, DD 298 356, and DD 298 357 teach a 3-step process for regenerating the catalyst bed in an ethylbenzene-to-styrene dehydrogenation comprising: (1) shutting down the reaction and substituting a steam feed for the mixed steam-ethylbenzene feedstream; (2) followed by a heat treatment step; and (3) followed by introducing potassium ions in a steam feed (for example by vaporizing KOH or $K_2CO_3$). None of these patents, however, teach or suggest in situ catalyst regeneration without process interruption. The process of these German patents would be costly, cumbersome, and result in the kind of undesirable saw-tooth pattern mentioned above.

U.S. Pat. No. 4,551,571 (Sarumaru et al.) teaches a different approach for extending the life of the catalyst bed in an ethylbenzene-to-styrene dehydrogenation comprising the method of employing two kinds of potassium-containing dehydrogenation catalysts arranged in a particular way within the catalyst bed. U.S. Pat. No. 4,590,324 (Satek) is broadly directed to dehydrogenation of an alkylaromatic compound containing at least two carbon atoms and at least one alkyl group (for example, ethylbenzene) to an alkenylaromatic (such as styrene) by contact with a particular catalyst. Satek's preferred catalyst comprises copper on a support of aluminum borate. At col. 6, lines 57–63, Satek teaches that the catalyst "can be treated or doped with an alkali metal or alkaline earth metal compound for use in the dehydrogenation." Such a one-time doping step is taught as being particularly advantageous for conversion of ethylbenzene to styrene. At col. 6, line 64–col. 7, line 18, Satek also teaches that the oxides, hydroxides and salts of potassium, among others, are suitable agents for doping the catalysts. Satek further teaches that aqueous solutions of the doping agent can be added to feedstocks going to a reactor. However, Satek only suggests doping his particular catalyst (copper on aluminum borate) in the preceding manner. Comparable teachings appear in U.S. Pat. No. 4,645,753 (Zletz et at.), which is referred to as a copending patent application at col. 6, lines 61–63 of Satek.

U.S. Pat. No. 4,902,845 (Kim et al.) teaches a process for extending the life of an iron oxide containing catalyst in alkyl aromatic dehydrogenation processes consisting of adding oxygen or oxygen precursors (such as peroxides) to the reactant feedstream for in situ treatment of the catalyst bed without interruption of the dehydrogenation process. But, the examples and test data presented in Kim et al. demonstrate that this procedure is not really very effective. Indeed, FIG. 1 of Kim et al. suggests that the Kim et al. process at most slows, but does not reverse, the degradation of the dehydrogenation catalyst.

U.S. Pat. Nos. 4,451,686 (DeClippeleir et al.), 5,190,906 (Murakami et al.), 4,064,187 (Soderquist et al.), 4,277,369 (Courty et al.), and 4,287,375 (Moller et al.), are all directed to various embellishments of the conventional ethylbenzene-to-styrene catalytic dehydrogenation process. DeClippeleir et al., for example, suggests one mechanism by which catalyst regeneration might occur in teaching that a small amount of an alkali metal oxide, particularly potassium oxide, "promotes the removal of coke and tars by reaction with steam through the water-gas reaction, and mitigates therefore a carbon build-up on the catalyst surface," (col. 1, lines 39–43). U.S. Pat. No. 4,737,595 (Jones et al.) does not relate specifically to ethylbenzene-to-styrene conversion but does address catalyst regeneration in a method for broadly dehydrogenating dehydrogenatable hydrocarbons. The aforementioned U.S. patents are incorporated herein by reference.

None of the foregoing patents, however, discloses any method for either regenerating or stabilizing catalyst activity in order to maintain substantially steady-state dehydrogenation conditions, over extended periods of time and at very high levels of conversion and selectivity without process interruption. These and other problems with and limitations of the prior art are overcome with the catalyst regenerating and/or stabilizing method and apparatus of this invention.

OBJECTS OF THE INVENTION

Accordingly, it is a principal object of this invention to provide a method of and apparatus for regenerating and/or stabilizing a dehydrogenation catalyst.

It is also an object of this invention to provide a method of and apparatus for regenerating a dehydrogenation catalyst in situ.

Another, more specific object of this invention is to provide a method of and apparatus for continuously or intermittently regenerating a dehydrogenation catalyst without process interruption and so as to maintain substantially steady-state reaction conditions at high levels of conversion and selectivity over extended time periods.

Still a further object of this invention is to provide an improved method for dehydrogenating ethylbenzene to styrene in the presence of a catalyst containing iron and one or more alkali metal compounds.

Specifically, it is an object of this invention to provide a method of and apparatus for regenerating and/or stabilizing a dehydrogenation catalyst containing iron and one or more alkali metal compounds by adding to the reactant feedstream an alkali metal compound.

Other objects of the invention will in part be obvious and will in part appear hereinafter. The invention accordingly comprises the methods, processes, and apparatus involving the several steps and the relation and order of one or more of such steps with respect to each of the others and to the apparatus exemplified in the following detailed disclosure, and the scope of the application of which will be indicated in the claims.

SUMMARY OF THE INVENTION

The dehydrogenation catalyst regeneration and/or stabilization method of this invention comprises the steps of continuously or intermittently adding to a reactant feedstream an effective amount of an alkali metal compound during continuation of the dehydrogenation process. The method of this invention may also include the step of gradually increasing the reaction zone temperature. The method of this invention can be utilized, for example in the catalytic dehydrogenation of ethylbenzene to styrene, to achieve substantially steady-state reaction conditions at high levels of conversion and selectivity.

DETAILED DESCRIPTION OF PREFERRED EMBODIMENTS

Figure 1:
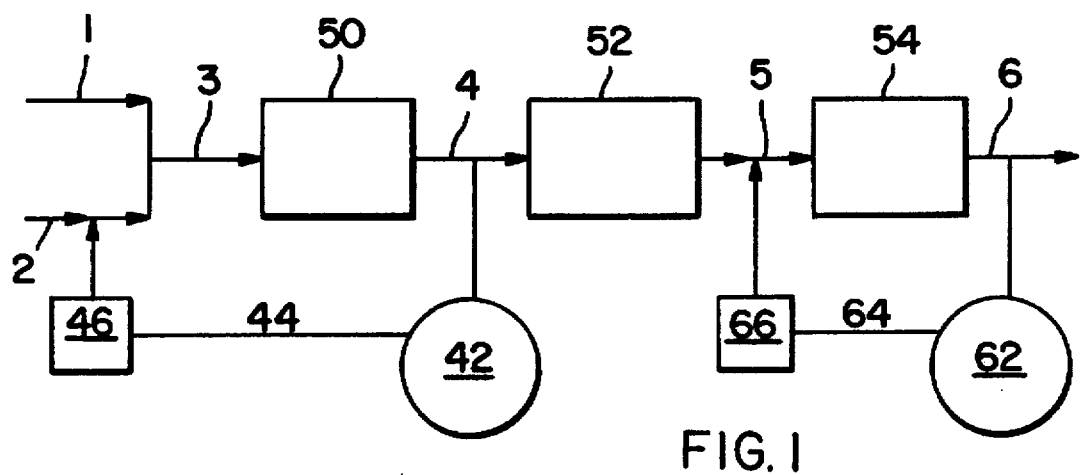
FIG. 1 is a schematic representation of one embodiment of the method and apparatus of this invention.

The method of this invention broadly comprises regenerating and/or stabilizing the activity of a dehydrogenation catalyst used in the catalytic dehydrogenation of an alkylaromatic hydrocarbon to obtain a specific desired alkenylaromatic hydrocarbon. Such dehydrogenation catalysts are well known in the art and are commercially available. In general, such catalytic dehydrogenation processes are carried out at temperatures ranging from about 400° C. to about 700° C., and preferably between about 500° C. to 700° C., by contacting a preheated feedstream, containing a mixture of the alkylaromatic hydrocarbon and steam, with a particular dehydrogenation catalyst. The process can be carried out in single or multistage reactors having fixed catalyst beds or in fluidized beds. The choice of starting alkylaromatic hydrocarbon, dehydrogenation catalyst, reaction temperature and proportion of alkylaromatic hydrocarbon to steam in the feedstream will affect, in part, the resulting alkenylaromatic hydrocarbon as well as the efficiency and selectivity of the conversion process.

In particular, using the aforementioned process, ethylbenzene is converted to styrene by contact with a dehydrogenation catalyst containing iron and at least one alkali metal compound. For example, the ethylbenzene-to-styrene conversion can be advantageously carried out at reaction temperatures ranging from about 500° C. to about 700° C., preferably from about 550° C. to about 650° C., and at reaction pressures ranging from about 3 to about 20 psia, preferably from about 5 to about 9 psia. The steam-to-hydrocarbon ratio in the reactant feedstream may range from a ratio of about 0.6:1 to about 3:1 steam to ethylbenzene by weight, preferably a ratio of about 1.0:1 to about 2.0:1 steam to ethylbenzene by weight. The space velocity may range from about 0.2 to about 1.2 kilograms of ethylbenzene per hour per kilogram of catalyst.

Beginning the ethylbenzene-to-styrene conversion process with fresh catalyst, following start-up there is typically an initial conditioning period lasting from about 3–45 days characterized by high initial activity followed by rapid deactivation. For example, during the initial conditioning period, the overall level of conversion of ethylbenzene to styrene might drop off to below about 55 mole % and the level of styrene selectivity might fall to below about 93 mole %. Thereafter in conventional ethylbenzene-to-styrene dehydrogenation processes, the level of catalyst activity continues to fall albeit at slower rates than during the initial conditioning period. In a multi-stage reactor, the level of conversion of ethylbenzene to styrene in each stage might drop by about one-third, for example, from about 30–36 mole % to about 20–24 mole %, during the initial conditioning period, and then continue to drop at a slower rate thereafter. The end of the initial conditioning period in this process generally can be identified by those skilled in the art as the point at which the slope of the line plotting conversion level over time flattens out. As noted previously, the prior art has suggested a number of possible explanations for the gradual deterioration of catalyst activity, but no single mechanism seems to fully account for this phenomenon.

Whatever the explanation, the continued process deterioration beyond the initial conditioning period leads to a number of problems and disadvantages. First, the efficiency of the conversion process is reduced. Unreacted ethylbenzene must be separated from the other components of the output stream for recycling. Styrene must similarly be separated from the unreacted ethylbenzene as well as from other reaction products. Second, instead of a relatively uniform output stream having relatively constant ratios of styrene, ethylbenzene and miscellaneous by-products, process deterioration leads to an output stream of ever-changing composition. Third, at some point, the level of conversion or the level of styrene selectivity or both fall sufficiently low that the process is no longer economically viable. At this point, the process would have to be shut down and the catalyst either replaced or regenerated by conventional means.

One technique for maintaining the conversion level of ethylbenzene to styrene is to raise the reaction temperature. This can be accomplished, for example, by increasing the temperature of the reactant stream or by adding heat to the reactor chamber. The reaction temperature can be increased slowly and substantially continuously or it can be increased periodically in increments. The impact of such reaction temperature increases is to increase the rate of reaction in order to offset the continuing deterioration of catalyst activity. But, there are relatively narrow limits to the utility of this temperature-raising technique. In particular, above a certain temperature, the mechanical temperature limit of the catalyst or the equipment is approached. Beyond this point, further temperature increases lead to degradation of the catalyst's physical structure and degradation of equipment integrity. As the aforedescribed limit is approached, therefore, the process would have to be shut down and the catalyst either replaced or regenerated by conventional means. Although this temperature-raising technique extends catalyst life somewhat and can be utilized (for example, through continuous or small, frequent reaction temperature increases) to maintain relatively constant conversion of ethylbenzene for a limited period of time, by itself it is of limited utility for the reasons stated.

By contrast, the method of this invention is capable of restoring and/or stabilizing the activity of the catalyst and consequently extending the life of the catalyst far beyond what can be achieved with conventional processes. More particularly, the method of this invention is capable of restoring the activity of the dehydrogenation catalyst to substantially the same high levels of conversion and selectivity as those established at the end of the initial conditioning period. The method of this invention is also capable of stabilizing the activity of the catalyst at those same high levels of conversion and selectivity for extended periods of time beyond those achievable with conventional processes. The method of this invention may also be utilized in tandem with the aforedescribed temperature-raising technique for additional benefits of further increasing the catalyst life or increasing the ethylbenzene conversion. The method of this invention broadly comprises the steps of continuously or intermittently adding to a reactant feedstream of an alkylaromatic hydrocarbon an effective amount of an alkali metal compound sufficient to regenerate, stabilize, or enhance the activity of the dehydrogenation catalyst and thereby to restore and to maintain high levels of conversion and selectivity. The term "maintain" as used herein is intended to be construed to mean—to keep in a state of repair, efficiency or validity; to preserve from failure or decline over a protracted period of time, e.g. for many months or years. The method is of particular utility in connection with regenerating and/or stabilizing a dehydrogenation catalyst containing iron and at least one alkali metal compound. Such dehydrogenation catalysts are well known in the art and some of those that are available commercially include: the S6-20, S6-21 and S6-30 series from BASF Corporation; the C-105, C-015, C-025 and C-035 series from Criterion Catalyst Company, L.P.; and the G-64 and G-84 series (including catalyst G-84C used in Examples 1–4 hereinafter) from United Catalysts, Inc. These catalysts typically contain 40–80% $Fe_2O_3$, 5–30% $K_2O$, and other promoters. All of such and similar catalysts are considered within the scope of this invention.

The method of this invention can be used in connection with the catalytic dehydrogenation of virtually any alkylaromatic hydrocarbon to a corresponding alkenylaromatic hydrocarbon. The appropriate combination of alkylaromatic hydrocarbon, catalyst and reaction conditions in order to obtain a particular desired alkenylaromatic hydrocarbon is generally well known in the art and, in any event, would be a matter of choice and routine experimentation. The method of this invention is of particular utility in connection with regenerating and/or stabilizing a dehydrogenation catalyst in the process of converting ethylbenzene to styrene.

Dehydrogenation of ethylbenzene to styrene over an iron oxide catalyst system provides a useful illustration of the method of this invention. Dehydrogenation of ethylbenzene to styrene typically is accomplished commercially with an iron oxide catalyst promoted with potassium compounds in the presence of excess superheated steam.

Catalysts useful in this invention are those containing an oxide of iron. Preferably, a substantial portion of such iron oxide is in the form $Fe_3O_4$, although $Fe_2O_3$ may be reduced in situ by hydrogen to $Fe_3O_4$. Usually, further reduction to FeO leads to an inactive catalyst species. Other materials can be present in minor amounts as promoters or stabilizers. Examples of such added materials are nonoxidation catalytic compounds of Groups IA, IB IIA, IIB, IIIA, VB, VIB, VIIB and VIII and rare earths, such as zinc oxide, magnesium oxide, chromium or copper salts, potassium oxide, potassium carbonate, oxides of chromium, manganese, aluminum, vanadium, magnesium, thorium and molybdenum. For example, an iron oxide catalyst useful in this invention may contain about 50 to about 95 wt. % iron red as $Fe_2O_3$, about 5 to about 30 wt. % potassium compound, measured as potassium oxide, such as potassium carbonate and potassium oxide and up to about 20 wt. % of other compounds, measured as their oxides, such as compounds of vanadium, cadmium, magnesium, manganese, nickel, rare earths, chromium, and mixtures thereof. Preferable iron oxide-containing catalysts contain about 70 to about 90 wt. % iron oxide (as $Fe_2O_3$) about 5 to about 30 wt. % potassium compound (as $K_2O$) and up to about 20 wt. % other compounds measured as their oxides. One specific example of an iron oxide-containing catalyst suitable for ethylbenzene dehydrogenation contains about 80–90 wt. % iron oxide (as $Fe_2O_3$), about 8–15 wt. % potassium oxide, about 1–3 wt. % chromium oxide and about 0–1 wt. % vanadium oxide.

Compounds which catalyze oxidation of hydrocarbons, such as platinum or palladium salts, should be substantially absent from iron oxide-containing catalysts used in this invention.

Various iron oxide-containing catalysts and processes using such catalysts have been reported widely. Examples of such catalysts and processes include U.S. Pat. Nos. 2,111, 726; 2,408,140; 2,414,585; 2,426,829; 2,461,147; 2,870,228; 2,945,960; 3,084,125; 3,179,706; 3,179,707; 3,205,179; 3,291,756; 3,306,942; 3,361,683; 3,387,053; 3,424,808; 3,703,593; 3,849,339; 3,907,416; 4,039,601; 4,143,083; 4,144,197; and 4,152,300, all incorporated by reference herein. Commercially, suitable iron oxide catalysts are sold under trademarks such as Shell-105, Shell-115, Shell-015, UCI-G64D, UCI-G64E, UCI-G64F and UCI-G64I.

Conversion processes using iron oxide-containing catalysts include hydrocarbon dehydrogenation such as ethylbenzene to styrene, ethyltoluene to vinyltoluene, cumene to alpha-methylstyrene and butenes to butadiene. Other conversion processes are formation of gasoline fraction hydrocarbons from synthesis gas, dealkylaration of alkylaromatics such as toluene to benzene, and synthesis of ammonia from nitrogen and hydrogen. Broadly, conversion processes using iron oxide-containing catalysts are run at temperatures ranging from about 150° to about 1000° C. at pressure of about 0.01 to about 100 atmospheres (1–10,000 kPa) at liquid hourly space velocities of about 0.01 to about 10 $hr^{-1}$.

FIG. 1 is a flowchart that schematically illustrates one embodiment of the method of this invention wherein an alkali metal compound is added to an incoming feedstream as well as to the partially converted reactant stream passing between the stages of a multi-stage reactor. Although for purposes of discussing FIG. 1, the terms "feedstream" and "partially converted reactant stream" are used to help identify particular stages in the conversion process, elsewhere in this description these terms are considered generic and interchangeable. In FIG. 1, incoming feedstream 1 may be the feed of alkylaromatic hydrocarbon, for example ethylbenzene, and incoming feedstream 2 may be steam. As shown in FIG. 1, an effective amount of an alkali metal compound is added continuously or intermittently to feedstream 2 by alkali metal supply means 46. Alternatively, the alkali metal compound can be added to feedstream 1. Feedstreams 1 and 2, including any alkali metal compound, are combined into reactant stream 3 and directed to the inlet of reactor 50, which is loaded with a suitable dehydrogenation catalyst. Alternatively, the alkali metal compound can be added after feedstreams 1 and 2 have been combined into reactant stream 3 prior to reactor 50. Partial conversion of the alkylaromatic hydrocarbon, for example ethylbenzene to styrene, occurs in reactor 50.

The partially converted reactant stream or exit stream 4 emerging from reactor 50 is then passed through a reheater 52 to restore the heat lost in reactor 50 and to reestablish the optimum reaction temperature. Additional alkali metal compound from alkali metal supply means 66 is added continuously or intermittently to the partially converted reactant stream 5 emerging from the reheater 52 before reactant stream 5 is directed to the inlet of reactor 54. Alternatively, additional alkali metal compound can be added to the partially converted reactant stream 4 coming from reactor 50 before it enters the reheater. Reactor 54 is also loaded with a suitable dehydrogenation catalyst. Further conversion of the alkylaromatic hydrocarbon occurs in reactor 54. It will be apparent to those skilled in the art that additional downstream reactor stages, such as a third or a fourth stage, each loaded with a suitable catalyst, may be utilized to obtain still further conversion of the alkylaromatic hydrocarbon. Addition of alkali metal compound to the reactant stream in accordance with the method of this invention may be advantageously employed between some or all of the reactor stages in a multi-stage reactor.

As shown in FIG. 1, the apparatus of this invention may advantageously include monitoring means for monitoring the chemical composition of the exit streams coming from the outlets of any one or more of the reactor stages, such as monitoring means 42 and 62 associated respectively with reactant streams 4 and 6. The monitoring means may also advantageously be coupled to activating means, such as electrical wires 44 and 64 respectively, for signalling and activating alkali metal compound supply means, such as pump or injection means 46 and 66 respectively, located upstream from the subject reactor stage, namely reactor 50 and 54 respectively.

The monitoring means can be adapted through conventional technology to send a signal to the alkali metal compound supply means whenever the exit stream from the subject reactor stage falls below a predetermined level of conversion or selectivity, which indicates degradation of catalyst activity in the reactor stage. Upon activation by the signal from the associated monitoring means, the alkali metal compound supply means would begin to supply alkali metal compound at a predetermined rate to the associated feedstream or reactant stream. For example, on signal from monitoring means 42 that the conversion or selectivity in reactor 50 had dropped below a certain level, pump means 46 would begin to supply alkali metal compound to feedstream 2. The apparatus can be designed on activation to continue supplying alkali metal compound for a predetermined period of time or until another signal from the associated monitoring means signals that catalyst activity in the subject reactor stage has been restored to the desired activity level.

As an alternative to the automated, intermittent addition system described above, it is also within the scope of this invention to continuously add alkali metal compound to the respective feedstreams or reactant streams. This may be combined with continuous or intermittent monitoring of one or more reactor stage exit streams. Upon signs of catalyst degradation in any reactor stage, means for increasing the addition of alkali metal compound to a feedstream or reactant stream upstream from the subject reactor stage can be manually activated. The increased rate of addition of alkali metal compound can be for a limited period of time until the desired catalyst activity level is restored or else it can be maintained at the new, higher rate.

Figure 2:
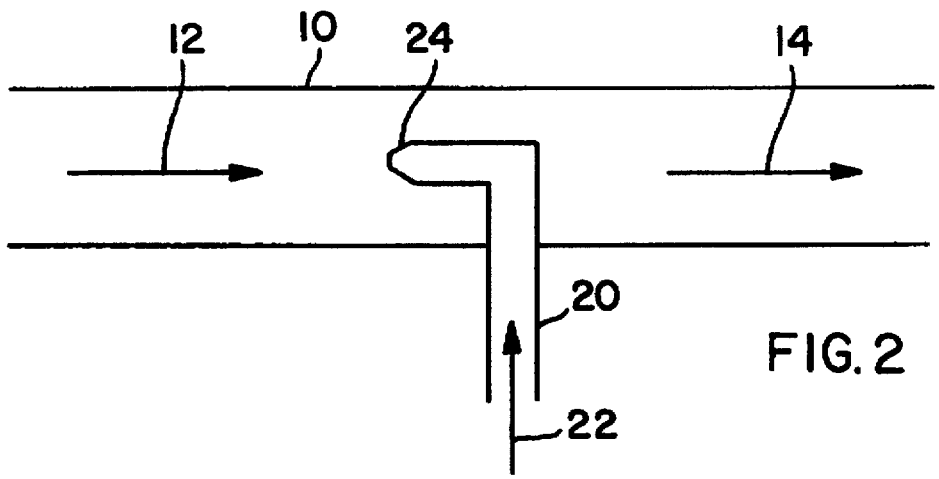
FIG. 2 illustrates a preferred method and associated apparatus for carrying out the alkali metal compound addition step of this invention.

FIG. 2 schematically illustrates in somewhat greater detail one preferred method and associated apparatus for adding alkali metal compound to a feedstream or a reactant stream in accordance with this invention. Conduit 10 in FIG. 2 contains and directs stream 12 in the direction of a reactor stage containing dehydrogenation catalyst as illustrated by the arrows. Stream 12 may represent, for example, feedstreams 1 or 2, the combined reactant stream 3, or partially converted reactant streams 4 and 5 as shown in FIG. 1. Alkali metal compound is added continuously or intermittently to stream 12 in the form of aqueous solution 22 delivered through injection means 24 at the outlet end of an injection tube 20 fitted through an aperture in the wall of conduit 10. Stream 14, downstream from the outlet end of injection tube 20, represents a feedstream or a reactant stream that has been mixed with alkali metal compound in accordance with this invention.

Figure 3:
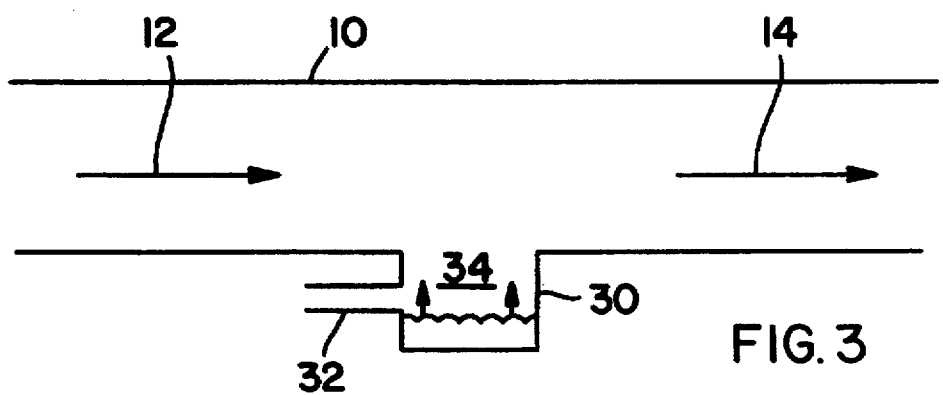
FIG. 3 illustrates an alternative method and associated apparatus for carrying out the alkali metal compound addition step of this invention.

FIG. 3 schematically illustrates an alternative method and associated apparatus for adding alkali metal compound to a feedstream or a reactant stream in accordance with this invention. Conduit 10 in FIG. 3 contains and directs stream 12 in the direction of a reactor stage containing dehydrogenation catalyst as illustrated by the arrows 12 and 14. Stream 12 may represent, for example, feedstreams 1 or 2, the combined reactant stream 3, or partially converted reactant streams 4 and 5 as shown in FIG. 1. Conduit 10 further defines an adjacent vessel 30 in open vapor communication with the flow path of stream 12 and capable of retaining solid or liquid matter. Alkali metal compound in a solid or liquid state is fed as necessary to the interior 34 of vessel 30, through feed 32, so as to gradually vaporize and diffuse into the passing stream, as indicated by the arrows inside vessel 30. Stream 14, downstream from vessel 30, represents a feedstream or a reactant stream that has been mixed with alkali metal compound in accordance with this invention.

The alkali metal compounds that are useful in carrying out the method of this invention include all non-halogen sources of alkali metal ions. As used in connection with this invention, the term "alkali metal" is meant to include, but without limitation thereto, potassium, sodium, lithium and other less-common members of the group IA metals of the periodic table, such as rubidium and cesium. Cost considerations will ordinarily dictate the choice of a potassium or sodium compound, however. For some applications, members of the group IIA metals of the periodic table (e.g. magnesium, calcium, and so forth) may also have utility. Selection of an appropriate alkali metal compound is considered a matter of routine experimentation. In connection with the dehydrogenation of ethylbenzene to styrene, the preferred alkali metal compounds are potassium compounds, more particularly one or more compounds selected from the group consisting of potassium oxide, potassium hydroxide, and potassium carbonate. It is also within the scope of this invention to use mixtures of two or more alkali metal compounds. Because halogen ions, such as chloride, have typically been found to poison the dehydrogenation catalyst, alkali metal compounds such as potassium chloride should generally be avoided.

The amount of alkali metal compound to be added to a feedstream or reactant stream in accordance with this invention may vary depending upon the catalyst, the alkylaromatic hydrocarbon, the reaction conditions, and the alkali metal compound itself. An effective amount or an effective rate of addition of alkali metal compound to the reactant stream sufficient to maintain high levels of conversion and selectivity can be determined by routine experimentation in order to optimize system performance. In general, it has been found that an effective amount of the alkali metal compound comprises from about 0.01 to about 100 parts by weight of alkali metal compound per million parts of the reactant stream, preferably from about 0.10 to about 10 parts by weight, on average over a representative time frame. A representative time frame as used herein means that period of time during which high levels of conversion and selectivity are maintained without further addition of alkali metal compound. It is also within the scope of this invention to vary the amount of alkali metal compound in the reactant stream over time to restore or to maintain optimum system performance.

The alkali metal compound may be added to the reactant stream either continuously or intermittently and, if intermittently, at regular or irregular intervals. Where the alkali metal compound is added intermittently, the amounts added and the intervals selected should be such to insure addition of an effective amount sufficient to restore or to maintain high levels of conversion and selectivity. In general, such amounts will comprise from about 0.01 to about 100 parts weight of alkali metal compound per million parts of the reactant stream on average over a representative time frame.

The addition of the alkali metal compound to the reactant stream may be accomplished in a number of ways. One such addition method is to add the alkali metal compound in dry, solid, powdered form to a reactant stream. Alternatively, a solid lump of or a vessel containing the alkali metal compound can be placed in the path of the heated reactant stream and allowed to gradually vaporize into the passing stream. Another and particularly preferred addition method is to add the alkali metal compound in the form of an aqueous solution into a reactant stream, for example as described above in connection with FIG. 2. Because of ease of handling and the ability to automate the process, as described in connection with FIG. 1, the addition of alkali metal compound in the form of an aqueous solution will probably normally be the preferred commercial application of this invention. Still another addition method is to inject the alkali metal compound in a liquid form into the reactant stream. Still another addition method is to pre-vaporize the alkali metal compound and inject the vapor into the reactant stream.

The method of this invention will be better understood by reference to the following examples and test data, which are illustrative only and are not limiting of the scope or practice of this invention.

EXAMPLE 1

Steam and ethylbenzene at a molar ratio of 12 to 1 and a rate of 825 grams/hr was introduced into a reactor constructed with one inch schedule 40 stainless steel pipe and was heated in an 8-zone electrical oven. A total of 390 grams of a catalyst designated as G-84C and manufactured by United Catalysts, Inc., was loaded in the reactor in four sections. The reactor was packed with inert alumina balls on top of the first catalyst zone, between catalyst zones, and below the fourth zone. The reaction mixture entered the reactor at a temperature of 250° C. and was preheated to 598° C. as it entered into the first catalyst section. The average temperature of the four catalytic sections was kept within 1° C. of 594° C. The reactor outlet was maintained at atmospheric pressure. Deactivation of catalyst was observed between 854 and 1298 hours on-stream time as shown in Table 1 below. The styrene selectivity increased slightly during this period due to decline in ethylbenzene conversion. At 1310 hours, the test unit was shut down and a stainless steel container loaded with 5.4 grams of ACS grade KOH was placed on top of the alumina. After the reactor was restarted, a small amount of KOH vaporized continuously and was brought into contact with catalyst by the reactor feed stream. The temperature at the container was controlled such that KOH vapor pressure was equivalent to about 5 ppm (by weight) of total feed. The activity and selectivity of the catalyst were found to improve continuously between 1310 and 1500 hours. The catalyst activity then remained stable at about 2.3 percentage points higher in conversion and about 0.3 percentage points higher in styrene selectivity than before addition of KOH. At 1642 hours, the ethylbenzene conversion with KOH addition was 4.4 percentage points higher than what it would have been at the same on-stream time had the catalyst deactivated at the same rate of KOH. The introduction of KOH. The styrene selectivity with KOH addition was 0.4 percentage points higher than that without KOH when compared with data at comparable ethylbenzene conversion (e.g., that at 854 hours).

TABLE 1

| | On-Stream Time (hours) | | | | | | | | | |
|---|---|---|---|---|---|---|---|---|---|---|
| | 854 | 874 | 1283 | 1298 | 1476 | 1506 | 1535 | 1563 | 1620 | 1642 |
| KOH (ppm) | 0 | 0 | 0 | 0 | 5 | 5 | 5 | 5 | 5 | 5 |
| Overall Conversion (mole %) | 61.7 | 61.7 | 59.3 | 59.2 | 60.9 | 61.5 | 61.4 | 61.5 | 61.5 | 61.6 |
| Overall Selectivity (mole %) | 96.6 | 96.7 | 96.9 | 96.7 | 96.9 | 97.0 | 97.0 | 97.0 | 97.1 | 97.1 |

EXAMPLE 2

A second reactor constructed and loaded similar to that described in example 1 was loaded with 32.5 grams of G-84C catalyst in the top zone. The reactor was operated at average temperatures between 594° and 612° C., steam-to-ethylbenzene ratio between 9 and 12, at an outlet pressure of 14.7 psia between 0 and 3341 hours. The ethylbenzene feed rate throughout the run was kept the same as that in example 1. Deactivation of the top zone catalyst was observed between 1722 and 1888 hours, as shown in Table 2 below, while the zone was kept within 1° C. of 597° C. The steam-to-ethylbenzene ratio was 12 molar. At 3341 hours, the unit was shut down and a superheater, which allowed loading of KOH into it later on without interrupting the reaction, was installed upstream of the reactor inlet. After the unit was restarted, the top zone catalyst continued to deactivate while it was kept within 1° C. of 622° C. (Table 2). The steam-to-ethylbenzene ratio was 9 and the reactor outlet pressure was 14.7 psia. At 3481 hours, 7.0 grams of ACS grade KOH was loaded into the superheater while the reaction was uninterrupted. The superheater temperature was controlled to allow small amounts of KOH to vaporize continuously and be brought into contact with catalyst by the reaction mixture. The vapor pressure of KOH at such temperature was equivalent to about 9 ppm (by weight) of total feed. The ethylbenzene conversion in the top zone improved rapidly from 5.1% to 12.3% in 103 hours while the zone was kept within 1° C. of 622° C., then increased gradually to 12.9% in 176 hours, and remained at such high level for 630 hours. This example illustrates that the catalyst which is immediately exposed to the feedstream is most susceptible to deactivation and also received the greatest benefit from the method of this invention.

TABLE 2

| | On-stream Time (hours) | | | | | | | | | | |
|---|---|---|---|---|---|---|---|---|---|---|---|
| | 1722 | 1800 | 1888 | 3347 | 3418 | 3473 | 3504 | 3584 | 3760 | 4132 | 4390 |
| KOH (ppm) | 0 | 0 | 0 | 0 | 0 | 0 | 9 | 9 | 9 | 9 | 9 |
| Top Zone Conversion (mole %) | 9.4 | 8.9 | 8.3 | 6.0 | 5.6 | 5.1 | 6.9 | 12.3 | 12.9 | 12.8 | 12.9 |

EXAMPLE 3

The reactor described in example 2 was run until the KOH in the superheater was depleted. The outlet pressure and the steam-to-ethylbenzene ratio were then adjusted to 6 psia and 8:1 molar, respectively. The top zone temperature was kept within 1° C. of 622° C. Ageing of the top zone catalyst was observed between 4731 and 5022 hours while the styrene selectivity was deteriorating. At 5022 hours, an additional 1.90 grams of KOH was loaded into the superheater and the superheater temperature was controlled to give a KOH vapor pressure equivalent to about 2 ppm (weight) of total feed. The top zone conversion went up from 9.2% to 11.4% in 24 hours, then stabilized at about 11.0% for an extended period of time while the top zone styrene selectivity improved from 94.8 to 96.8%, as shown in Table 3 below.

TABLE 3

| | On-stream Time (hours) | | | | | | | | | |
|---|---|---|---|---|---|---|---|---|---|---|
| | 4731 | 4925 | 5022 | 5026 | 5034 | 5046 | 5062 | 5114 | 5159 | 5204 |
| KOH (ppm) | 0 | 0 | 0 | 2 | 2 | 2 | 2 | 2 | 2 | 2 |
| Top Zone Conversion (mole %) | 11.0 | 9.6 | 9.2 | 10.1 | 11.1 | 11.4 | 11.0 | 11.1 | 11.1 | 11.0 |
| Top Zone Selectivity (mole %) | 95.0 | 94.8 | 94.8 | 94.5 | 95.1 | 96.4 | 96.7 | 96.9 | 96.8 | 96.7 |

EXAMPLE 4

In example 3, the average temperature of the four catalyst zones was kept within 1° C. of 613° C. The reactor outlet pressure was 6 psia, and the steam-to-ethylbenzene ratio was 8:1 molar. The overall conversion decreased from 70.4% to 69.3% between 4728 and 5019 hours before the second batch of KOH was loaded. The overall styrene selectivity was stable at 96.9%. After KOH was loaded into the superheater at 5022 hours, the overall conversion increased steadily from 69.3 to 70.4% in two days and remained above that high level subsequently. The styrene selectivity remained stable at 96.9% in this period, i.e., the same selectivity was observed at a higher conversion.

TABLE 4

| | On-stream Time (hours) | | | | | | | | | |
|---|---|---|---|---|---|---|---|---|---|---|
| | 4728 | 4860 | 4932 | 5019 | 5031 | 5047 | 5071 | 5121 | 5168 | 5211 |
| KOH (ppm) | 0 | 0 | 0 | 0 | 2 | 2 | 2 | 2 | 2 | 2 |
| Overall Conversion (mole %) | 70.4 | 70.1 | 69.7 | 69.3 | 69.8 | 70.2 | 70.4 | 70.4 | 70.5 | 70.5 |
| Overall Selectivity (mole %) | 96.9 | 96.9 | 96.9 | 96.9 | 96.8 | 96.9 | 96.9 | 96.9 | 96.9 | 97.0 |

The foregoing examples illustrate that the method of this invention is effective in restoring the activity of a partially deactivated catalyst and in stabilizing the conversion of ethylbenzene to styrene at a high level, while simultaneously maintaining or improving the selectivity to styrene.

Since certain changes may be made in the above-described apparatuses and processes without departing from the scope of the invention herein involved, it is intended that all matter contained in the above description shall be interpreted in an illustrative and not in a limiting sense.

Having described the invention, what we claim is:

1. Method of regenerating and stabilizing the activity of a dehydrogenation catalyst consisting essentially of iron oxide catalyst promoted with alkali metal while continuing the catalytic dehydrogenation of an alkylaromatic hydrocarbon to obtain an alkenylaromatic hydrocarbon comprising the steps of:
   (a) forming a mixed reactant stream consisting essentially of said alkylaromatic hydrocarbon, steam, and an effective amount of an alkali metal compound equivalent to a continuous addition of about 0.01 to about 100 parts per million by weight of alkali metal compound relative to the weight of the total alkylaromatic hydrocarbon and steam, said effective amount of alkali metal compound being sufficient to maintain substantially constant levels of catalyst activity; and (b) bringing said mixed reactant stream into contact with said dehydrogenation catalyst, while continuing the catalytic reaction beyond an initial catalyst conditioning period.

2. Method of claim 1 wherein said catalyst consists essentially of about 40–80% $Fe_2O_3$ and about 5–30% $K_2O$.

3. Method of claim 1 wherein said alkali metal compound is added continuously to said reactant stream.

4. Method of claim 1 wherein said alkali metal compound is added intermittently to said reactant stream.

5. Method of claim 1 wherein said alkylaromatic hydrocarbon is ethylbenzene and said alkenylaromatic hydrocarbon is styrene.

6. Method of claim 1, wherein said alkali metal compound is a potassium or sodium compound.

7. Method of claim 6 wherein said sodium or potassium compound is selected from the group consisting of sodium hydroxide, potassium hydroxide, sodium oxide, potassium oxide, sodium carbonate, potassium carbonate, and mixtures thereof.

8. Method of claim 1 wherein said alkali metal compound is potassium hydroxide.

9. Method of claim 1 wherein said alkali metal compound is added in dry, solid form to said reactant stream.

10. Method of claim 9 wherein a vessel containing said alkali metal compound is placed in the flow path of said reactant stream.

11. Method of claim 1 wherein said alkali metal compound is added in the form of an aqueous solution to said reactant stream.

12. Method of claim 1 wherein said alkali metal compound is added to said reactant stream as a vapor.

13. Method of claim 1 wherein said alkali metal compound is added to said reactant stream as a liquid.

14. Method of claim 1 wherein said catalytic dehydrogenation is carried out at substantially constant reaction temperature.

15. Method of claim 1 further comprising the step of gradually increasing the reaction temperature.

16. Method of claim 1 wherein said alkylaromatic hydrocarbon is a polyalkylated monoaromatic compound.

17. Method of claim 16 wherein said polyalkylated monoaromatic compound is ethyltoluene.

18. Method of claim 16 wherein said polyalkylated monoaromatic compound is diethylbenzene.

19. Method of claim 16 whereto said polyalkylated monoaromatic compound is methylethylbenzene.

20. Method of claim 16 wherein said polyalkylated monoaromatic compound is ethylxylene.

21. Method of claim 16 wherein said polyalkylated monoaromatic compound is ethyltrimethylbenzene.

22. Method of claim 1 wherein said alkylaromatic hydrocarbon is an alkylated biphenyl compound.

23. Method of claim 22 wherein said alkylated biphenyl compound is ethylbiphenyl.

24. Method of claim 22 wherein said alkylated biphenyl compound is ethyldimethylbiphenyl.

25. Method of claim 1 wherein said alkylaromatic hydrocarbon is an alkylated naphthalene compound.

26. Method of claim 25 wherein said alkylated naphthalene compound is ethylnaphthalene.

27. A method of regenerating and stabilizing the activity of a dehydrogenation catalyst, consisting essentially of iron oxide catalyst promoted with alkali metal, used in the catalytic dehydrogenation of an alkylaromatic hydrocarbon in a series of reactors containing said catalyst to obtain an alkenylaromatic hydrocarbon, said method comprising the steps of: adding to a feedstream consisting essentially of said alkylaromatic hydrocarbon reaction product from said reactors and steam an effective amount of an alkali metal compound equivalent to a continuous addition of about 0.01 to about 100 parts per million by weight of alkali metal compound relative to the weight of said feedstream, said effective amount being sufficient to maintain substantially constant levels of catalyst conversion and selectivity, to form a mixed reactant stream; and, directing said mixed stream into said reactor while continuing said catalytic conversion beyond an initial catalyst conditioning period of about 3–45 days.

28. Method of claim 27 wherein said catalyst consists essentially of about 40–80% $Fe_2O_3$ and about 5–30% $K_2O$.

29. Method of claim 27 wherein said alkali metal compound is added continuously to said feedstream.

30. Method of claim 27 wherein said alkali metal compound is added intermittently to said feedstream.

31. Method of claim 27 wherein said alkylaromatic hydrocarbon is ethylbenzene and said alkenylaromatic hydrocarbon is styrene.

32. Method of claim 27 wherein said alkylaromatic hydrocarbon is a polyalkylated monoaromatic compound.

33. Method of claim 32 wherein said polyalkylated monoaromatic compound is ethyltoluene.

34. Method of claim 32 wherein said polyalkylated monoaromatic compound is diethylbenzene.

35. Method of claim 32 wherein said polyalkylated monoaromatic compound is methylethylbenzene.

36. Method of claim 32 wherein said polyalkylated monoaromatic compound is ethylxylene.

37. Method of claim 32 wherein said polyalkylated monoaromatic compound is ethyltrimethylbenzene.

38. Method of claim 27 wherein said alkylaromatic hydrocarbon is an alkylated biphenyl compound.

39. Method of claim 38 wherein said alkylated biphenyl compound is ethylbiphenyl.

40. Method of claim 38 wherein said alkylated biphenyl compound is ethyldimethylbiphenyl.

41. Method of claim 27 wherein said alkylaromatic hydrocarbon is an alkylated naphthalene compound.

42. Method of claim 41 wherein said alkylated naphthalene compound is ethylnaphthalene.

43. Method of claim 27 wherein said alkali metal compound is a potassium or sodium compound.

44. Method of claim 43 wherein said sodium or potassium compound is selected from the group consisting of sodium hydroxide, potassium hydroxide, sodium oxide, potassium oxide, sodium carbonate, potassium carbonate, and mixtures thereof.

45. Method of claim 27 wherein said alkali metal compound is potassium hydroxide.

46. Method of claim 27 wherein said alkali metal compound is added in dry, solid form.

47. Method of claim 27 wherein said alkali metal compound in a solid or liquid state is placed in the flow path of said feedstream.

48. Method of claim 27 wherein said alkali metal compound is added in the form of an aqueous solution.

49. Method of claim 27 wherein said alkali metal compound is added as a vapor.

50. Method of claim 27 wherein said alkali metal compound is added as a liquid.

51. Method of claim 27 wherein said catalytic dehydrogenation is carried out at substantially constant reaction temperature.

52. Method of claim 27 further comprising the step of periodically increasing the reaction temperature.

53. A method of regenerating and stabilizing the activity of a catalyst consisting essentially of iron oxide catalyst promoted with alkali metal while continuing the catalytic conversion of synthesis gas to gasoline fraction hydrocarbons comprising the steps of: (a) forming a mixed reactant stream consisting essentially of said synthesis gas and an effective amount of an alkali metal compound equivalent to a continuous addition of about 0.01 to about 100 parts per million by weight of alkali metal compound relative to the weight of said reactant stream, said effective amount being sufficient to maintain high levels of conversion: and (b) bringing said mixed reactant stream into contact with said catalyst while continuing said catalytic conversion beyond an initial catalyst conditioning period.

54. A method of regenerating and stabilizing the activity of a catalyst consisting essentially of iron oxide catalyst promoted with alkali metal while continuing the catalytic dealkylation of an alkylaromatic hydrocarbon to obtain an aromatic hydrocarbon comprising the steps of:

(a) forming a mixed reactant stream consisting essentially of said alkylaromatic hydrocarbon and an effective amount of an alkali metal compound equivalent to a continuous addition of about 0.01 to about 100 parts per million by weight of alkali metal compound relative to the weight of said reactant stream, said effective amount being sufficient to maintain high levels of conversion; and (b) bringing said mixed reactant stream into contact with said catalyst while continuing said catalytic conversion to said aromatic hydrocarbon beyond an initial catalyst conditioning period.

55. Method of claim 54 wherein said alkylaromatic hydrocarbon is toluene and said aromatic hydrocarbon is benzene.

56. A method of regenerating and stabilizing the activity of a catalyst consisting essentially of iron oxide catalyst promoted with alkali metal while continuing the catalytic synthesis of ammonia from nitrogen and hydrogen comprising the steps of:

(a) forming a mixed reactant stream consisting essentially of said nitrogen and hydrogen and an effective amount of an alkali metal compound equivalent to a continuous addition of about 0.01 to about 100 parts per million of weight of alkali metal compound relative to the weight of said reactant stream, said effective amount being sufficient to maintain high levels of conversion: and (b) bringing said mixed reactant stream into contact with said catalyst while continuing the catalytic conversion to ammonia beyond an initial conditioning period.

* * * * *